United States Patent [19]

Hradek et al.

[11] Patent Number: 5,071,453
[45] Date of Patent: Dec. 10, 1991

[54] OXYGEN CONCENTRATOR WITH PRESSURE BOOSTER AND OXYGEN CONCENTRATION MONITORING

[75] Inventors: Richard W. Hradek, Davenport, Iowa; William P. Myers, Rock Island, Ill.; David N. Alftine, Bettendorf; Tuan Cao, Davenport, both of Iowa

[73] Assignee: Litton Systems, Inc., Davenport, Iowa

[21] Appl. No.: 598,588

[22] Filed: Oct. 19, 1990

Related U.S. Application Data

[63] Continuation of Ser. No. 413,985, Sep. 28, 1989, abandoned.

[51] Int. Cl.$^5$ .............................................. B01D 53/04
[52] U.S. Cl. .................................... 55/21; 55/26; 55/68; 55/75; 55/179; 55/270; 55/389
[58] Field of Search .................. 55/18, 20, 21, 25, 26, 55/58, 62, 68, 75, 161–163, 179, 270, 389

[56] References Cited

U.S. PATENT DOCUMENTS

| | | | |
|---|---|---|---|
| 3,922,149 | 11/1975 | Ruder et al. | 55/25 X |
| 4,272,265 | 6/1981 | Snyder | 55/179 X |
| 4,323,370 | 4/1982 | Leitgeb | 55/18 |
| 4,404,005 | 9/1983 | Hamlin et al. | 55/179 X |
| 4,428,372 | 1/1984 | Beysel et al. | 55/25 X |
| 4,496,376 | 1/1985 | Hradek | 55/179 X |
| 4,537,607 | 8/1985 | Rogers et al. | 55/179 X |
| 4,552,571 | 11/1985 | Dechene | 55/179 X |
| 4,636,226 | 1/1987 | Canfora | 55/179 X |
| 4,648,888 | 3/1987 | Rowland | 55/25 X |
| 4,673,415 | 6/1987 | Stanford | 55/21 |
| 4,681,099 | 7/1987 | Sato et al. | 55/179 X |
| 4,681,602 | 7/1987 | Glenn et al. | 55/179 X |
| 4,698,075 | 10/1987 | Dechene | 55/179 X |
| 4,732,587 | 3/1988 | Koch | 55/179 X |
| 4,737,170 | 4/1988 | Searle | 55/179 |
| 4,783,205 | 11/1988 | Searle | 55/179 X |
| 4,787,417 | 11/1988 | Windsor, Jr. | 55/179 X |
| 4,810,265 | 3/1989 | Lagree et al. | 55/26 |
| 4,869,733 | 9/1989 | Stanford | 55/21 |

FOREIGN PATENT DOCUMENTS

| | | | |
|---|---|---|---|
| 0250235 | 12/1987 | European Pat. Off. | 55/25 |
| 2197801 | 6/1988 | United Kingdom | 55/25 |

*Primary Examiner*—Robert Spitzer
*Attorney, Agent, or Firm*—Brian L. Ribando

[57] ABSTRACT

In an oxygen concentrator which is intended for aircraft use, a booster compressor is used to increase the pressure of the product gas from the concentrator in order to increase the amount of the gas which can be stored in a plenum. The booster includes two moving pistons which are rigidly linked together and a series of check valves which control the flow of gases through the compressor. One of the pistons is driven by air from the rotary valve in the concentrator, and the other piston compresses the product gas for delivery to the plenum.

A small sample of concentrator product gas is monitored by an oxygen sensor for oxygen concentration. Once the oxygen concentration has reached an acceptable level the booster compressor fills the plenum with product gas. Thereafter, if oxygen concentration of product gas delivered to the crew from the concentrator falls below the concentration which is required at a particular altitude, the product gas stored in the plenum is delivered to the crew. The oxygen sensor monitors the concentrator output product gas to the breathing regulator when the stored plenum gas is not being used.

24 Claims, 7 Drawing Sheets

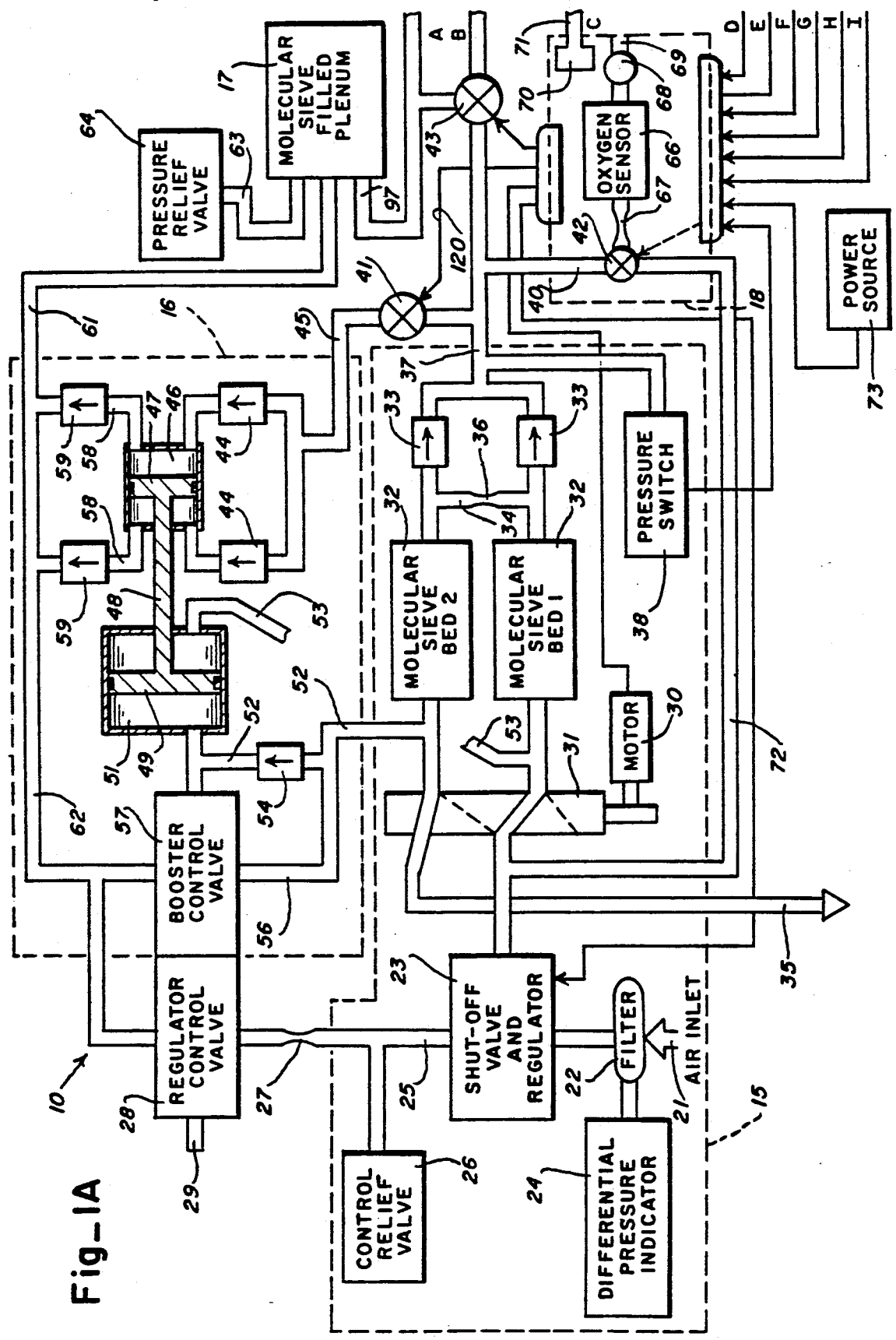
Fig_1A

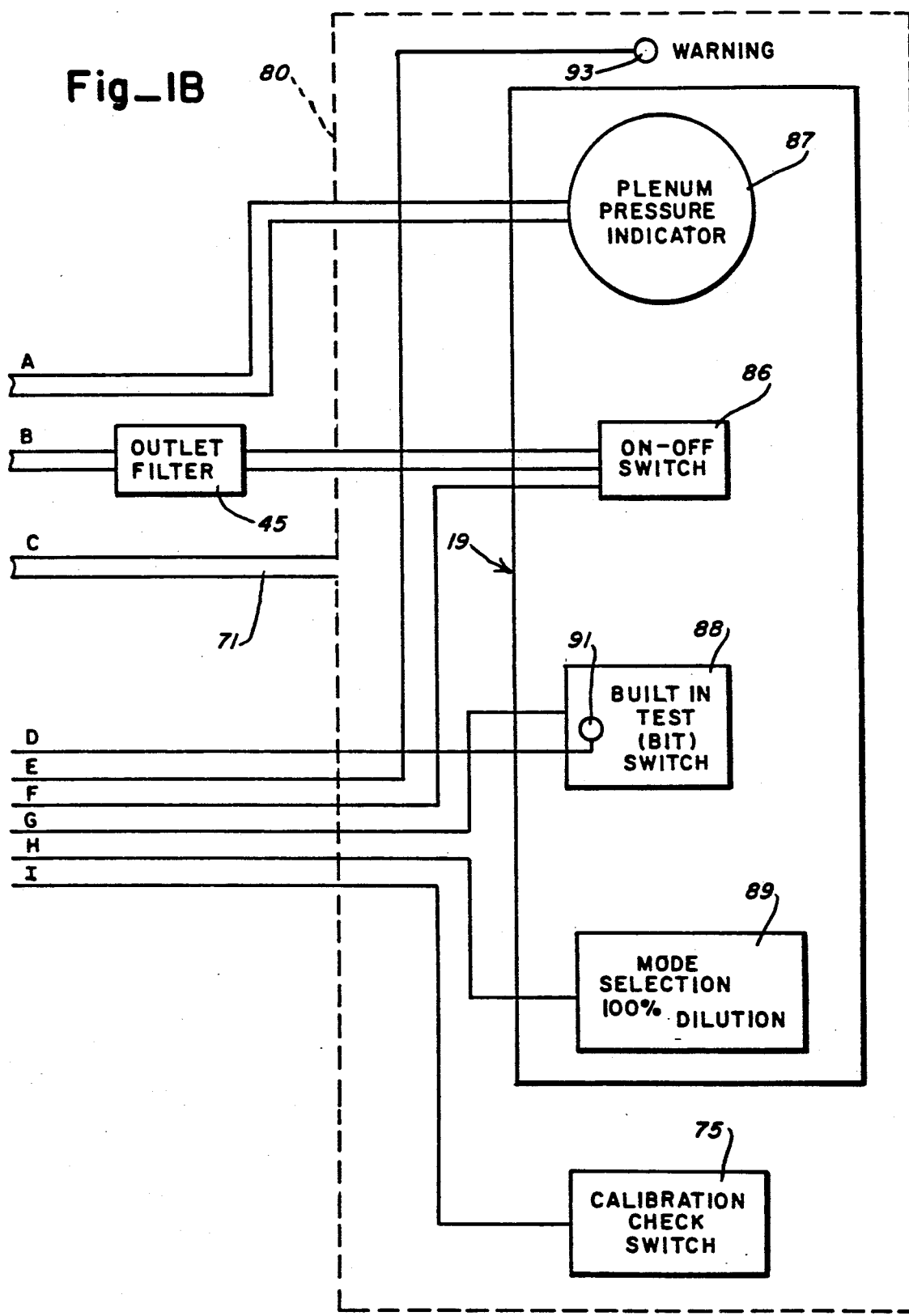
Fig_1B

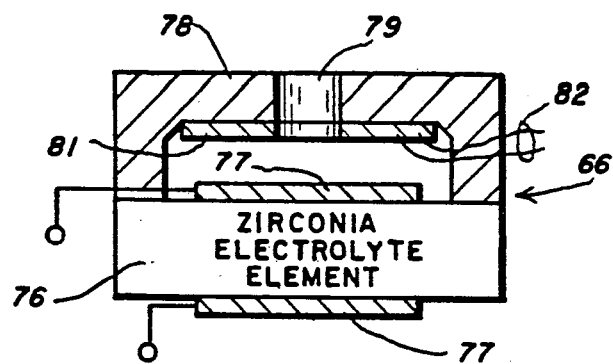
Fig_2
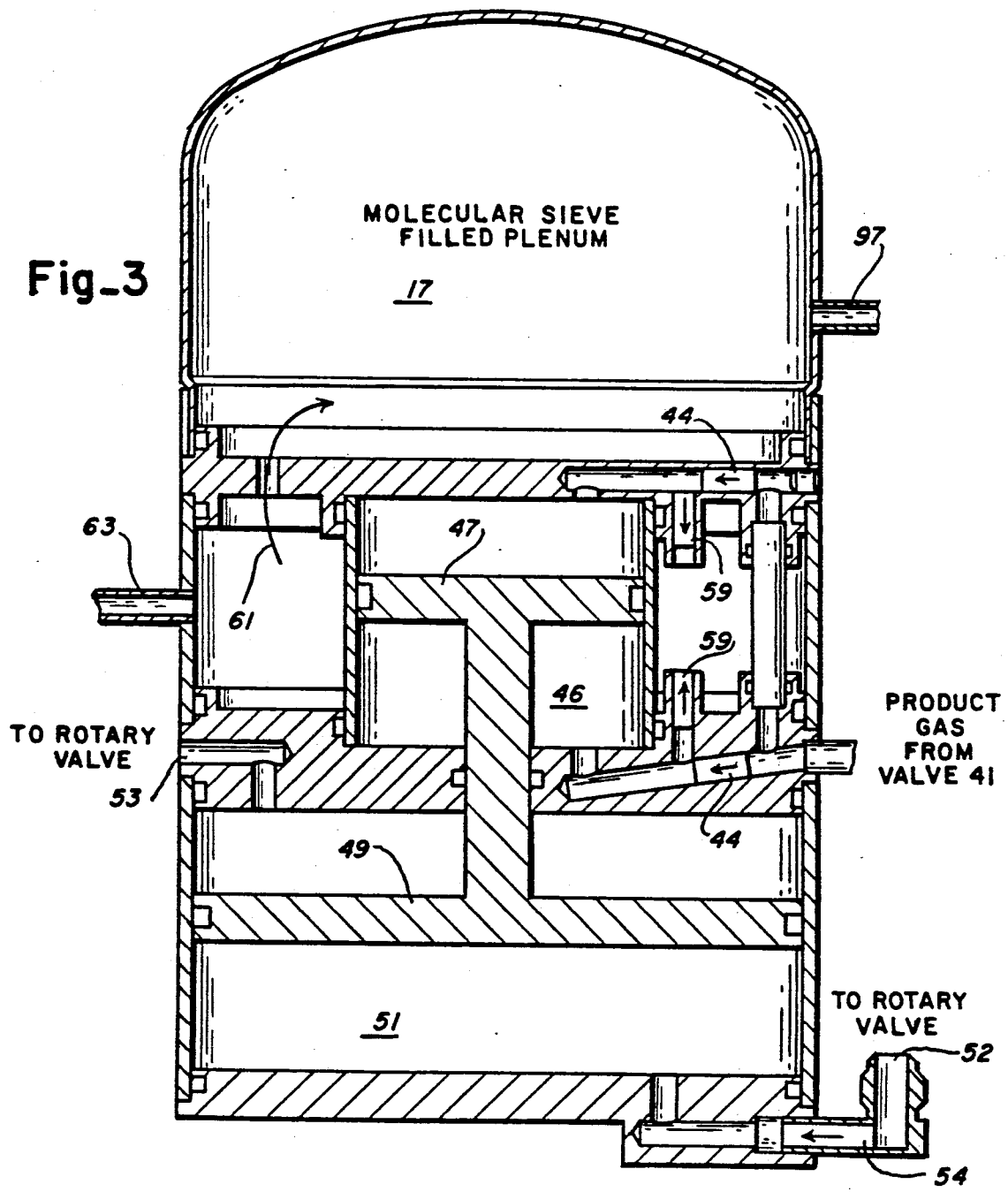
Fig_3

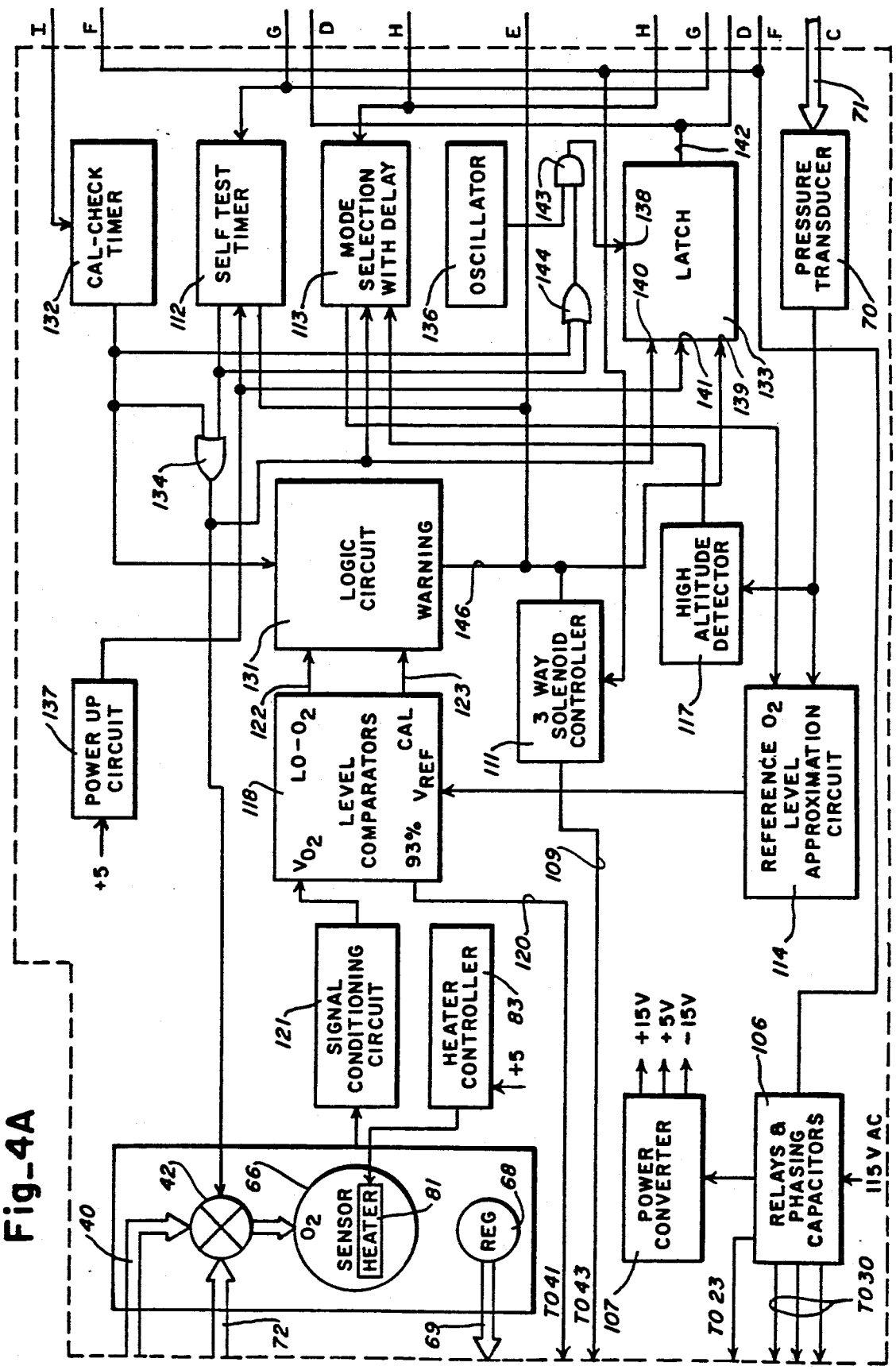
Fig_4A

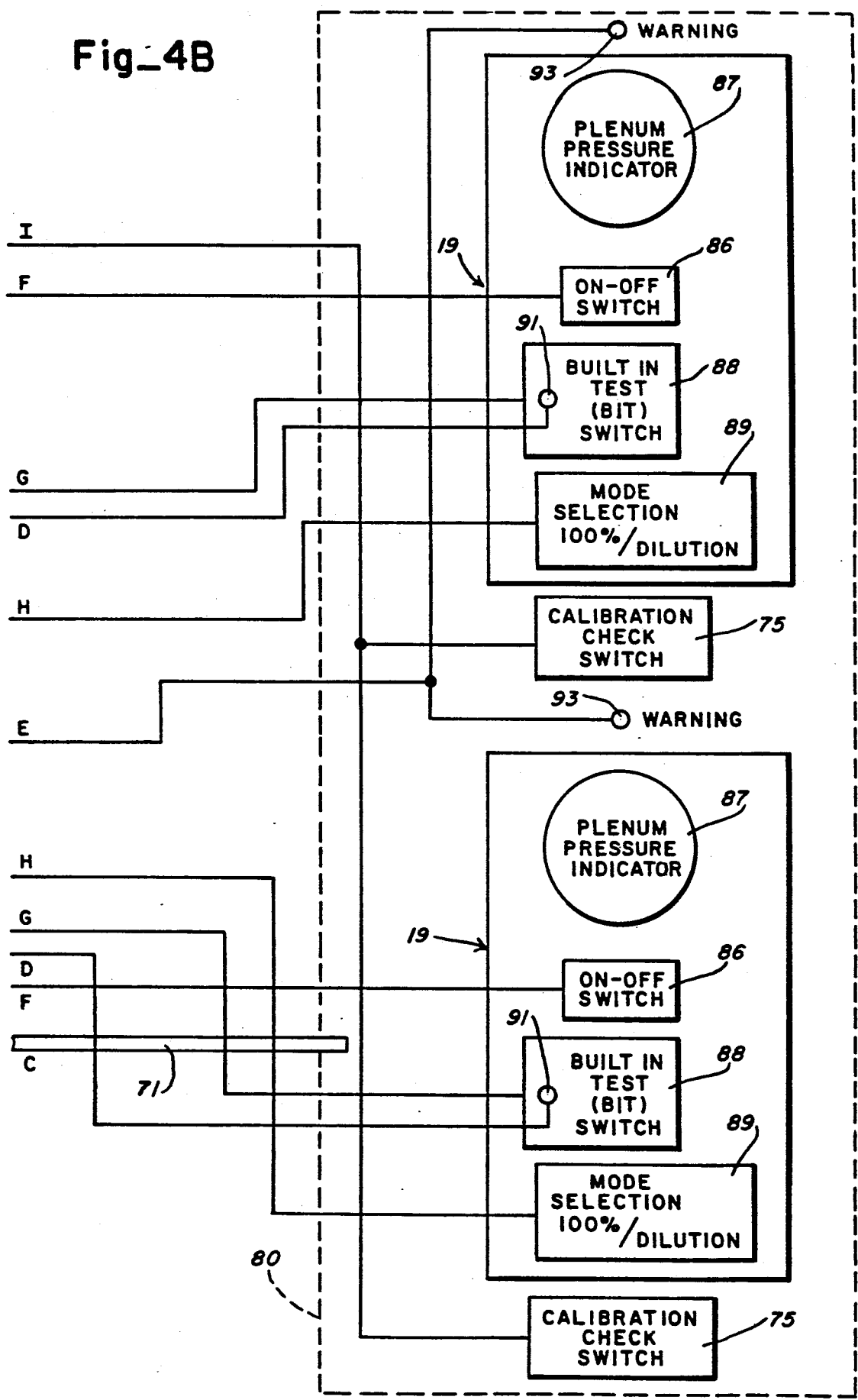
Fig_4B

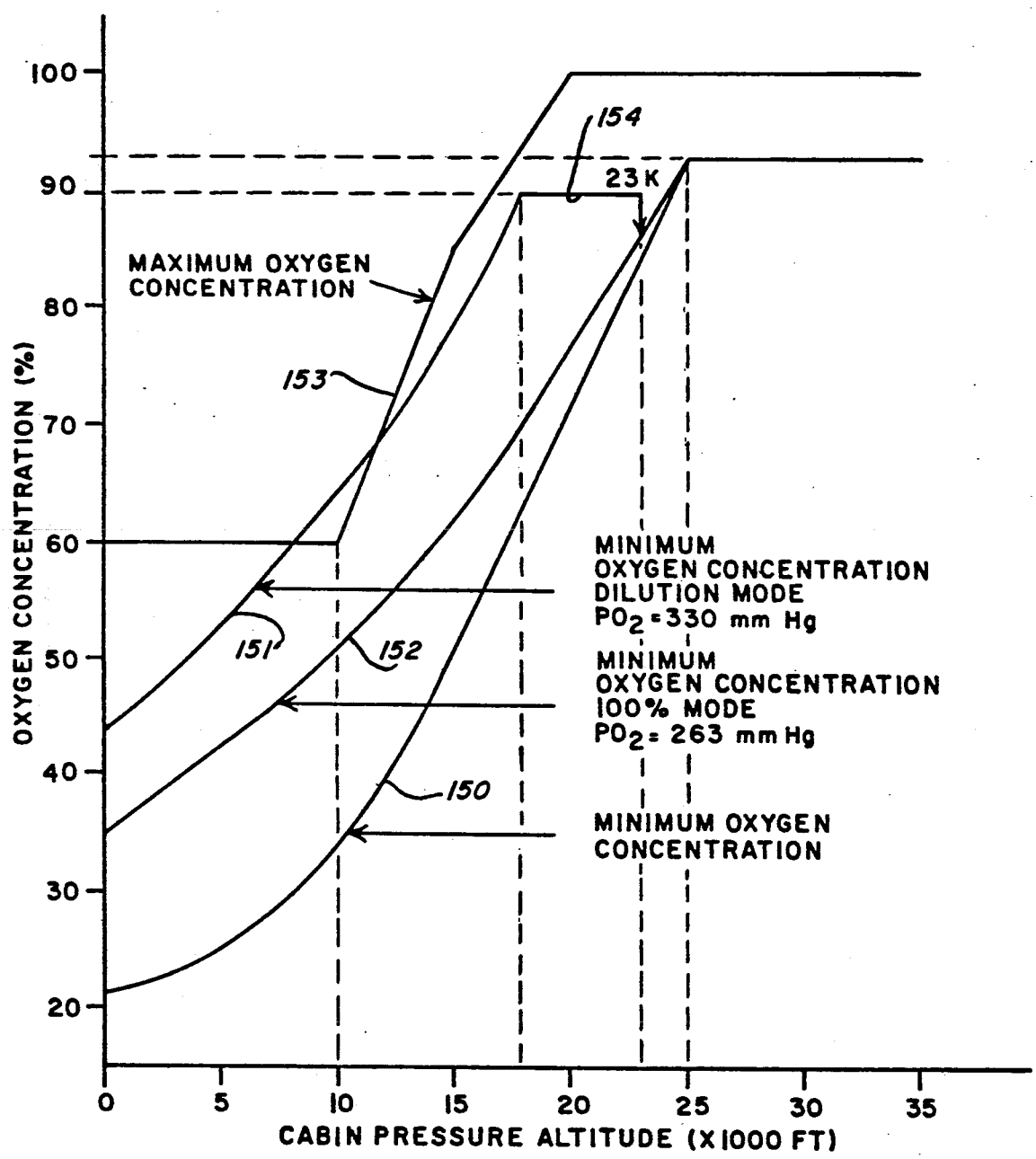
Fig_5

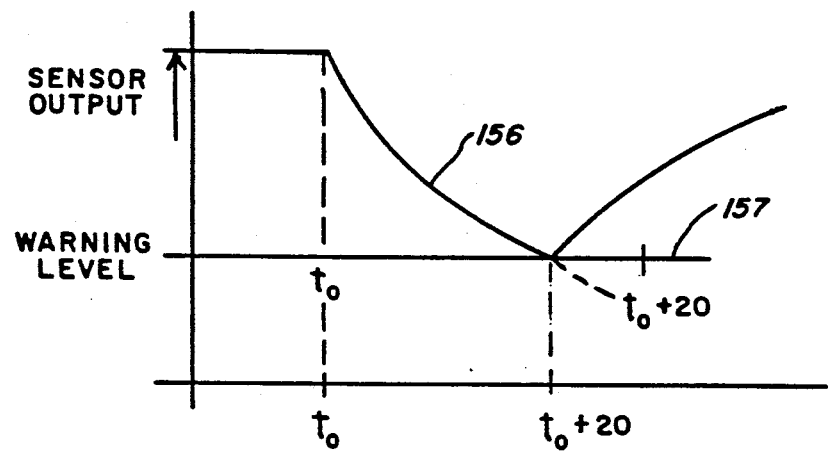
Fig_6
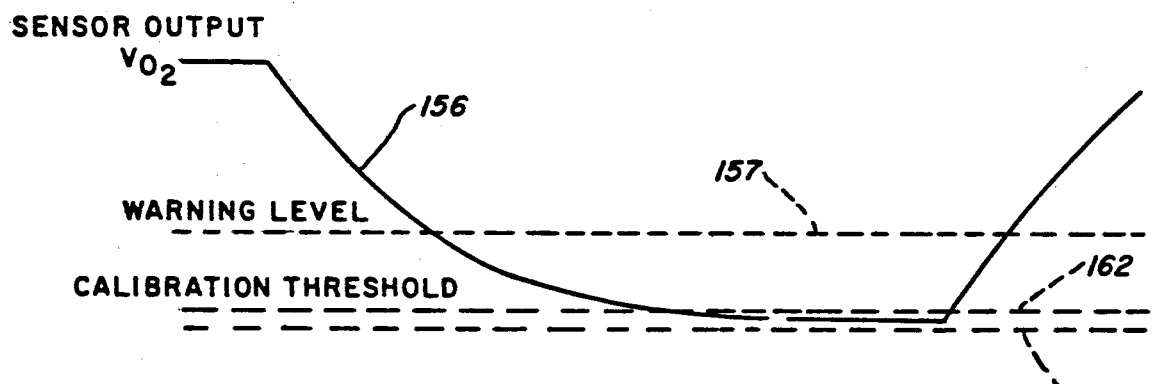
Fig_7

OXYGEN CONCENTRATOR WITH PRESSURE BOOSTER AND OXYGEN CONCENTRATION MONITORING

This is a continuation of copending application Ser. No. 07/413,985 filed on Sept. 28, 1989, now abandoned.

BACKGROUND OF THE INVENTION

This invention relates to a pressure swing adsorption apparatus for generating oxygen-enriched product gas in which a booster compressor pressurizes the product gas for storage in a plenum and an oxygen sensor monitors the concentration of oxygen in the product gas.

The use of the pressure swing adsorption technique for producing an oxygen-enriched product gas is well known. Pressurized air is sequentially delivered to a plurality of beds of molecular sieve material, and the nitrogen in the air becomes adsorbed by the sieve while the oxygen passes through. The beds are cyclically vented to atmosphere and back flushed with product gas to desorb and discharge the nitrogen from the molecular sieve; and in this fashion, a continuous flow of oxygen-enriched product gas can be generated. Such devices are also known as oxygen concentrators.

In an aircraft environment, an oxygen concentrator may be used to provide product gas to the crew for high altitude flying. In the event of concentrator failure due to loss of electrical power or pressurized air, or a motor or valve failure in the concentrator, a backup oxygen system (BOS) is provided to deliver oxygen for a period of time which will allow the aircraft to descend to an altitude where a supply of breathing oxygen is not required. In such systems, the BOS may be a molecular sieve filled plenum which is charged with product gas by the concentrator. Because of space restrictions in fighter aircraft, the physical size of the BOS is limited; and it may be impossible to store an adequate supply of breathing gas in the BOS at concentrator output pressure to sustain the crew during descent.

For example, an 8 minute supply of breathing gas for a crew of two at a flow rate of 26 liters per minute may be required. If the outlet pressure of the concentrator is in the range of 60 psig, it is impossible to store a sufficient quantity of product gas in the space normally allocated to the BOS. Consequently, a pressure intensifier or booster compressor may be used to increase the pressure of product gas delivered to the BOS so that a reasonably sized storage plenum will be able to contain the required amount of product gas.

Prior art booster compressors have required cycling devices which consist of shuttle valves. The shuttle valve is pneumatically driven and controlled by two pilot valves which are activated by a driver piston. These components are subject to wear and add increased complexity and cost to the concentrator unit.

It is also desirable to provide automatic controls which will fill the BOS plenum with concentrator product gas only when the oxygen content of the product gas is high and will switch the crew member's breathing gas supply from the concentrator output to the BOS when the oxygen content of the concentrator output is low. This requires an oxygen sensor which provides an accurate indication of oxygen concentration and is suitable for use in the temperature and pressure environment of an aircraft.

SUMMARY AND OBJECTS OF THE INVENTION

According to the invention, a booster compressor is used to increase the pressure of the product gas from a concentrator in order to increase the amount of the gas which can be stored in a plenum. The booster comprises two moving pistons which are linked together and a series of check valves which control the flow of gases through the compressor. One of the pistons is driven by compressed air from the rotary valve in the concentrator, and the other piston compresses the product gas for delivery to the plenum.

A small sample of concentrator product gas is monitored by an oxygen sensor for oxygen concentration. Once the oxygen concentration has reached an acceptable level for use at all altitudes, product gas from the concentrator flows to the booster compressor and fills the plenum. Thereafter, if oxygen concentration of product gas delivered to the pilot from the concentrator falls below the concentration which is required at a particular altitude, the stored gas in the plenum is delivered to the crew.

It is accordingly an object of the invention to provide an oxygen concentrator with a booster compressor for increasing the pressure of the product gas in a plenum to increase the amount of gas which can be stored in the plenum.

It is another object of the invention to provide an oxygen concentrator with an oxygen sensor for monitoring the oxygen concentration of the product gas.

It is another object of the invention to provide an oxygen concentrator with a backup oxygen supply for delivering oxygen when the oxygen concentration of the product gas from the concentrator falls below an acceptable level such as occurs when the concentrator fails or there is loss of electrical power or air supply to the concentrator.

It is still another object of the invention to provide an oxygen concentrator with an oxygen sensor to control the filling of a plenum when the oxygen concentration of product gas is above an acceptable level and to control delivery from the plenum when the oxygen content of product gas from the concentrator is below an acceptable level.

These and other objects of the invention will become apparent from the following description taken in conjunction with the accompanying drawing figures in which reference numerals used on the drawings correspond to those used throughout the description.

BRIEF DESCRIPTION OF THE DRAWINGS

FIGS. 1A and 1B show a schematic illustration of an oxygen concentrator and a panel mounted regulator according to the invention.

FIG. 2 is a sectional view of an oxygen sensor used in the invention.

FIG. 3 is a sectional view of a booster compressor with an adjacent plenum chamber.

FIGS. 4A and 4B show a schematic illustration showing the electrical circuitry of the monitor controller of the concentrator and the panel mounted regulator.

FIG. 5 shows the oxygen concentration curves which govern the operation of the monitor controller.

FIG. 6 shows the output of the oxygen sensor during a Built-In-Test.

FIG. 7 shows the output of the oxygen sensor during a calibration check.

DESCRIPTION OF THE PREFERRED EMBODIMENT

FIG. 1A shows a concentrator and booster assembly generally designated by the reference numeral 10. The concentrator assembly 10 comprises a concentrator unit 15, a pressure booster 16, a BOS storage plenum 17, and a monitor controller 18. The concentrator assembly 10 is coupled to one or more panel mounted regulators 19 shown in FIG. 1B by a plurality of pneumatic and electric lines. It will be understood by those skilled in the art that each panel mounted regulator 19 is coupled to masks (not shown) which deliver product gas to the crew.

As shown in FIG. 1A, the concentrator unit 15 comprises an air inlet 21 coupled to a filter 22 and a shut-off valve and regulator 23. A differential pressure indicator 24 is coupled to the filter 22 and to a line 25 including a control relief valve 26, and a flow restrictor 27. A regulator control valve 28 with a vent 29 senses the pressure in the plenum 17 as more fully described below and is coupled to the flow restrictor 27, the control relief valve 26, and the regulator 23.

An electrical motor 30 drives a rotary valve 31 which alternately directs air to the two beds 32 of molecular sieve material. The outlets of the beds 32 are coupled to check valves 33 and a purge line 34 including a flow restrictor 36; the inlets of the beds 32 are alternately coupled to a purge vent 35 by the rotary valve 31. The check valves 33 are coupled to the concentrator outlet 37 and to a pressure switch 38.

The concentrator outlet is coupled to a two-way BOS-Fill solenoid valve 41, a line 40, a three-way Self-Test solenoid valve 42 in the monitor controller 18, and a three-way Product-Delivery solenoid valve 43 coupled to an outlet filter 45 (seen in FIG. 1B). The BOS-Fill solenoid valve 41 is coupled by a line 45 to two check valves 44 which admit product gas to the compression cylinder 46 of the pressure booster 16. A compression piston 47 in the compression cylinder 46 is coupled by a rod 48 to a larger driver piston 49 in a driver cylinder 51. The driver cylinder 51 alternately receives air from the rotary valve 31 by means of two lines 52 and 53, one of which includes a check valve 54 and a vent line 56 coupled to a booster control valve 57. Two outlets 58 from the compression cylinder 46 are coupled to check valves 59 and to a booster outlet 61. A pressure tap 62 from the booster outlet 61 is coupled to the booster control valve 57 and to the regulator control valve 28. The booster outlet 61 is coupled to the plenum 17, to a pressure relief valve 64 through a pressure tap 63 and through a conduit 97, to the Product-Delivery solenoid valve 43, and to a pressure indicator 87 in the panel mounted regulator 19.

The monitor controller 18 includes the Self-Test solenoid valve 42 which is coupled to an oxygen sensor 66 through a flow restrictor 67 and is vented to ambient through an absolute pressure regulator 68 and a vent 69. A pressure transducer 70 is coupled to the cockpit 80 by means of a pressure sensing line 71, and an air line 72 couples the Self-Test solenoid valve 42 to the inlet of the rotary valve 31. The monitor controller 18 is coupled to a power source 73, and to a calibration check switch 75, a Built-In-Test (BIT) switch 88, a Mode Selection Switch 89 and an ON-OFF switch 86 located in the cockpit 80 (FIG. 1B). The monitor controller sends signals to a warning light 93 in the cockpit 80 which indicates both low oxygen and low pressure, and to the shut-off valve and regulator 23, the motor 30 for the rotary valve 31, the BOS-Fill solenoid valve 41, and the Product-Delivery solenoid valve 43. A more detailed description of the monitor controller 18 is given in conjunction with the description of FIGS. 4-7.

Turning now to FIG. 1B, the panel mounted regulator 19, the warning light 93, and the calibration check switch 75 are all mounted in the cockpit 80. The panel mounted regulator 19 includes the ON-OFF switch 86, the plenum pressure indicator 87, the BIT switch 88 with a BIT light 91, and a Mode Selection Switch 89.

Turning now to FIG. 2, the oxygen sensor 66 in the monitor controller 18 is shown in greater detail. The oxygen sensor 66 includes a zirconia electrolyte element 76 comprising $ZrO_2$-$Y_2O_3$ and having electrodes 77 attached to either side thereof. A hollow cap 78 having a diffusion hole 79 is mounted on the element 76, and a heater 81 having leads 82 for attachment to a power source is mounted on the cap 78.

Turning now to FIG. 3, the pressure booster 16 is shown immediately adjacent to the molecular sieve filled plenum 17. The plenum 17 is fitted with a conduit 97 for the removal of product gas as required and for connection to additional plenum volume at either adjacent or remote locations. As shown, the diameter of the driver piston 49 is greater than the diameter of the compression piston 47 to accomplish the compression of the product gas in the compression cylinder 46 by the air delivered to the driver cylinder 51 by the rotary valve.

FIG. 4A and 4B show the monitor controller 18 and the connections to the panel mounted equipment in the cockpit 80 in greater detail. Two or more regulators 19 may be provided and an ON-OFF switch 86 on each regulator 19 is coupled to a network of relays and phasing capacitors 106 which in turn is coupled to a power converter 107. The relays and phasing capacitors 106 are coupled to the shut off valve 23 and the motor 30 for the rotary valve 31 shown in FIG. 1. The power converter 107 provides +5 volt and ±15 volt power to various portions of the concentrator where needed. The ON-OFF switch 86 is also coupled to a three-way solenoid controller 111 which in turn is coupled by a line 109 to the three-way solenoid valve 43 seen in FIG. 1.

A Built-In-Test switch 88 is coupled to a self-test timer 112 having a time period of 20 seconds and a light 91 on the switch is coupled to a latch 133. A Mode selector switch 89 is coupled to a mode selection with Delay 113, which in turn is coupled to a reference $O_2$ level approximation circuit 114. The level approximation circuit 114 is additionally coupled to the pressure transducer 70 which measures the pressure in the cockpit 80 through the sensing line 71 and develops a signal representative of aircraft cockpit altitude. The output of the pressure transducer 70 is also coupled to a high altitude detector 117. The level approximation circuit 114 is coupled to a network of level comparators 118 which receives a signal from the oxygen sensor 66 through the signal conditioning circuit 121. The oxygen sensor 66 receives either product gas or air through the three-way solenoid valve 42 and is vented to ambient through the regulator 68. The oxygen sensor 66 includes the heater 81 which is powered through a heater controller 83.

The level comparator network 118 provides a control signal on line 120 to the two-way solenoid valve 41 which controls the filling of the plenum 17, as well as a low oxygen signal on line 122 and a calibration signal on line 123 to a logic circuit 131. The logic circuit 131 is coupled to the calibration check switch 75 through the calibration check timer 132. The logic circuit 131 provides a warning signal on line 146 to the three-way solenoid controller 111, to the warning light 93 in the cockpit, and to a latching circuit 133. The latching circuit 133 has a first input 138 coupled to the output of an AND gate 143, a second input 139 coupled to the warning output 146 of the logic circuit 131, a latch input 140, and a negative latch input 141. The output 142 of the latch 133 is coupled to the BIT lights 91 in the cockpit. The inputs of the AND gate 143 are coupled to the oscillator 136, and the output of the OR gate 144 and the inputs of the OR gate 144 are coupled to the CAL-CHECK timer 132 and the self-test timer 112. The output of the OR gate 134 is also coupled to the three-way solenoid valve 42. The self-test timer 112 is coupled to a power up circuit 137 which has inputs coupled to the power converter 107.

Turning now to FIG. 5, the curve 150 shows the minimum oxygen output requirements for the system in either, dilution mode (less than 100 percent concentrator output) or the 100 percent mode (pure oxygen) as a function of altitude. The curve 151 shows minimum oxygen concentration to the regulator as a function of altitude for a system output in the dilution mode which is maintained at an oxygen partial pressure (PO$_2$) of 330 mm Hg. The curve 152 shows minimum oxygen concentration as a function of altitude for a system output in the 100 percent mode which is maintained at 263 mm Hg PO$_2$. The curve 153 shows the maximum oxygen which may be delivered by the system in the dilution mode.

FIG. 6 shows the voltage output VO$_2$ of the oxygen sensor 66 as a function of time during the Built-In-Test. The voltage output curve 156 falls below the warning level 157 within the 20 second test period to show that the system is functioning properly.

FIG. 7 shows the voltage output VO$_2$ of the oxygen sensor as a function of time during a calibration check. The curve 156 falls below the warning level 157 and enters the calibration threshold between the limits 162 and 163 during the 2 minute test period.

OPERATION OF THE CONCENTRATOR

Pressurized air is coupled to the inlet 21, filtered to remove moisture and particulate matter in the filter 22, pressure regulated by the regulator 23, and ducted to the rotary valve 31. The regulator 23 maintains the pressure of the air to the rotary valve 31 at one of two pressures, depending on whether or not the booster 16 is operating to pressurize the product gas in the plenum 17 as more fully explained below. The rotary valve 31 alternately feeds the pressurized air to the beds 32 of molecular sieve, and oxygen-enriched product gas passes through the check valves 33 to the concentrator outlet 37. A portion of the product gas from one of the beds 32 passes through the flow restrictor 36 to back flush through the other bed in order to desorb nitrogen therefrom and vent the same to ambient through the purge vent 35.

OPERATION OF THE BOOSTER

The booster driving piston 49 is driven by air from the concentrator rotary valve 31. Referring to FIG. 1A when the rotary valve is charging molecular sieve bed 1, air pressure from the line 53 forces the driver piston to the left. At the same time, the rotary valve allows the air on the other side of the piston 49 to escape through the valve 57, the line 56, and the purge vent 35. At the same time, product gas from the valve 41 enters the compressor cylinder 46 through the right-hand inlet check valve 44, and the compressor piston 47 compresses the product gas which flows through the left-hand outlet 58, the check valve 59, and the booster outlet 61 to the product gas storage plenum 17. After completion of the stroke, the booster pump will delay the return stroke until the rotary valve 31 starts charging sieve bed 2; and air through line 52 and valve 54 will force the driver piston 49 to the right. This will compress another charge of product gas on the right side of compressor piston 47. Thus, each stroke of the piston 47 to the left or to the right compresses product gas and is a compression stroke.

As long as the two-way solenoid valve 41 stays open, this process will continue until the plenum is fully charged. If the two-way solenoid valve 41 closes, no product gas will flow to the compressor cylinder 46; and no additional product gas will be stored in the plenum 17. The maximum plenum pressure is limited by the pressure relief valve 64 and is determined by both the peak inlet air pressure and the ratio of the size of the driver piston 49 to the compressor piston 47. When the maximum plenum pressure is reached, the pressure booster is automatically shut off to conserve inlet air which is not needed as long as the BOS 17 remains fully charged. The booster is shut off by the increased plenum pressure in the lines 61 and 62 forcing the booster control valve 57 to a closed position, thus preventing the left side of the driver cylinder 51 from venting. The piston 49 then remains at the right side of the booster chamber until the plenum pressure drops, thus opening the shut-off valve 57 and resuming pressure cycling of the driver piston 49. This arrangement insures that the plenum stays fully charged with pressurized gas.

In actual practice, it has been found that increasing the pressure of the product gas in the molecular sieve filled plenum by a factor of approximately 5 increases the storage capacity of the plenum by a factor of approximately 3. Those skilled in the art will recognize that although the proportional storage capacity increase of the sieve filled plenum at increased pressure is not as great as the proportional capacity increase of a plenum at increased pressure without sieve, the total capacity of the sieve filled plenum at increased pressure is greater than the total capacity of a plenum without sieve at increased pressure.

The regulator control valve 28 is mechanically linked to the booster control valve 57; and when the booster control valve 57 closes because the plenum 17 is fully charged, the regulator control valve 28 vents pressure regulator air pressure from line 25 to ambient through the vent 29. The regulator control valve 28 is coupled to the shut-off valve and regulator 23 by the line 25, and ordinarily, the pressure in the line 25 controls the operation of the regulator 23. When the regulator control valve 28 closes the vent 29, the pressure in the line 25 will build to about 30 psig at which point the pressure is relieved by the relief valve 26. This allows the regulator 23 to regulate at about 55 psig. When control valve 28 opens the vent 29 to ambient, however, the regulator 23 will regulate at 25 psig.

This operation provides product gas at the concentrator outlet 37 at slightly less than 55 psig for pressurizing by the booster 16 and storage in the plenum 17, and reduces air consumption by the concentrator by reducing the concentrator bed inlet pressure to 25 psig when the plenum 17 is fully charged and at the same time shutting the booster off.

OPERATION OF THE OXYGEN SENSOR

The active element in the oxygen sensor, the zirconia electrolyte element 76, is a solid state current limiting oxygen sensor which is commercially available; but since the output of the element varies with temperature and pressure, modifications are necessary in order to obtain satisfactory performance in an aircraft environment. The heater 81 is used to maintain the element 76 at an operating temperature range of 400° C. to 600° C., independent of ambient temperature and it has been determined that a temperature close to 600° C. is preferable, since the response of the sensor is faster at the higher temperature. The flowrate of product gas to the sensor 66 is controlled by the flow restrictor 67 to isolate the oxygen sensor 66 from sudden and periodic pressure variations which may exist at the concentrator outlet 37. The absolute pressure regulator 68 is vented to ambient by the vent 69 and maintains a constant pressure at the sensor in order to avoid ambient pressure dependent fluctuation in the sensor output caused by changes in altitude.

In operation, a voltage potential applied to the electrodes 77 causes oxygen ions to conduct through the element 76 to provide an electro chemical pumping of the oxygen ions, and a limiting current is developed through the element 76 which at a constant temperature is proportional to the net diffusion rate of oxygen molecules through the diffusion hole 79. At the constant pressure which is maintained by the regulator 68, the diffusion rate of oxygen molecules is a function of oxygen concentration of the gas from the valve 42.

OPERATION OF THE SOLENOID VALVES 41, 42, AND 43

The output current of the oxygen sensor 66 is processed to give a voltage which is a function of oxygen concentration in the product gas admitted to the sensor 66 from the concentrator outlet 37. This voltage is compared by the level comparator 118 in the monitor controller 18 to reference levels to activate the control and warning signals. For example, a 93 percent $O_2$ reference voltage may be used to control the plenum filling two-way solenoid valve 41. The solenoid valve 41 is energized to allow flow through the compressor 16 to the plenum 17 when the product gas oxygen concentration is above 93 percent. The warning light 93 is lit when the oxygen concentration is below the minimum value for pilot breathing requirements as measured by the sensor 66, or when low pressure at the concentrator outlet 37 trips the switch 38. The Product-Delivery valve 43 is de-energized to provide product gas to the crew from the plenum 17 in order to provide fail-safe operation in the event of electrical failure.

The Self-Test solenoid valve 42 is ordinarily de-energized and conducts product gas from the concentrator output 37 to the oxygen sensor 66. In order to test the operation of the oxygen sensor 66, depression of the Built-In-Test button 88 or the calibration check switch 75 causes the solenoid valve 42 to admit air through the line 72 from the rotary valve 31 to the oxygen sensor 66. Once the test has been completed the self-test valve 42 is returned to its normal state allowing product gas to flow to the sensor 66.

OPERATION OF THE MONITOR CONTROLLER

Whenever the concentrator product gas oxygen concentration is below required minimum levels, the oxygen monitor controller 18 activates the warning light 93 and de-energizes the three-way solenoid valve 43 to deliver breathing gas to the pilot from the stored gas in the BOS 17. The control scheme is fail safe in that the two-way valve 41 closes and the three-way valve 43 automatically provides flow to the pilot from the plenum 17 during emergency conditions, (loss of electrical power, low oxygen, etc.).

Referring to FIG. 4, two diluter demand breathing regulators 19 control and regulate the breathing gas supplied to the pilot's mask. The regulators 19 are electrically connected to the oxygen concentrator assembly and the setting of the OFF-ON switch 86 on the regulators control actuation of the system. With both switches 86 in the OFF position, the regulators are closed to maintain pressure in the plenum 17, and the oxygen concentrator assembly is unpowered. Switching either regulator to the ON position applies power to the concentrator assembly through the relays 106 and the power converter 107 and allows the pilot with the ON regulator to breathe from the plenum 17 until the composition of the concentrator product gas at the oxygen sensor 66 is above the appropriate levels for the dilution and 100 percent breathing modes described below. The monitor controller 18 then energizes the three-way solenoid valve 43 to provide breathing gas to the pilots directly from the oxygen concentrator. The system includes a low-pressure switch 38 coupled to the output of the concentrator which, through the controller, turns on the warning light 93 and provides breathing gas from the BOS 17 in response to low pressure at the concentrator inlet 21 or a clogged inlet filter 22.

The product gas oxygen concentration is measured by the zirconia solid-state oxygen sensor shown in FIG. 2. The output of the oxygen sensor is processed by the signal conditioning circuit 121 and compared to the appropriate reference levels in the level comparators 118 and if appropriate to activate the warning signal and specific control functions.

When the built-in-test (BIT) is used for either the self-test or calibration check, the logic circuit 131 receives the low oxygen signal 122 and the calibration signal 123 from the level comparator 118, and the latch circuit 133 latches the result at the end of the BIT operation. The BIT light 91 flashes during a test, and a warning signal on line 146 illuminates the warning light 93 if the unit fails the self-test or calibration check. The warning signal 146 goes to the off condition and the BIT light 91 goes out when the unit passes the test.

The output signal of the oxygen sensor 66 is processed by the signal conditioning circuit 121 to give a voltage as a function of the product gas oxygen concentration. This voltage is compared in the level comparator 118 to reference levels programmed into the level comparator 118 to activate the control and warning signals. A 93 percent oxygen reference voltage is used to regulate filling of the plenum by the two-way solenoid valve 41. The solenoid valve 41 is energized by the control line 120 from the level comparator 118 to allow flow to the plenum 17 when the product gas oxygen concentration is above 93 percent.

Referring to FIG. 5, control and warning levels are provided following the curves 152 and 151. In the preferred embodiment, the minimum oxygen concentration to be delivered by the system in either the dilution or the 100 percent mode is 21 percent at sea level and 93 percent above 25,000 feet. Between sea level and 25,000 feet, the curve 150 defines the minimum. The curve 153 defines the maximum oxygen concentration which may be delivered by the system in the dilution mode.

The curve 152 is a plot of oxygen concentration vs. altitude for a constant oxygen partial pressure of 263 mm Hg. It will be seen that the oxygen concentration levels defined by the curve 152 at all altitudes are greater than the oxygen concentration levels defined by the curve 150 at the same altitudes. Accordingly, the curve 152 can be followed in order to deliver oxygen at a concentration which is always greater than the minimum shown by curve 150. Since the partial pressure of oxygen is the product of the oxygen concentration multiplied by the total pressure ($PO_2 = \%O_2 \times P$), the $\%O_2$ can be determined by dividing fixed $PO_2$ signal by the cabin pressure signal derived from the pressure transducer 70. This reference Level Limit is compared to the measured $\%O_2$ Level in the Level comparators 118; and if the measured product is less than 263 mm Hg, a low $O_2$ signal 122 is sent to the logic circuit 131.

The curve 151 is a plot of oxygen concentration vs. altitude for a constant oxygen partial pressure of 330 mm Hg. This curve is used as a lower limit for oxygen concentration in product gas supplied to the panel regulator 19 when the system is operating in the dilution mode, and accordingly, the addition of air by the regulator to the breathing mixture will reduce the oxygen concentration of the gas actually delivered to the crew.

It has been determined that the addition of air by the regulator will not reduce the oxygen concentration to a value below the minimum shown by the curve 150. As in the explanation of system operation in the 100 percent mode given immediately above, the $\%O_2$ value corresponding to 330 mm Hg can be determined by dividing the fixed reference $PP_{O2}$ signal by the altitude signal derived from the pressure transducer 70. This reference $\%O_2$ Level is compared to the measured $\%O_2$ in the level comparator 118; and if the measured product is less than 330 mm Hg $PPO_2$, a low $O_2$ signal 122 is sent to the logic circuit 131.

In the dilution mode, below 23,000 feet cabin altitude the reference levels follow the 330 mm Hg $PO_2$ curve 151 or 90 percent oxygen curve 154, whichever is less as shown in FIG. 5.

Above 23,000 feet, the 100 percent mode reference levels are used since the breathing regulators 19 automatically switch over to the 100 percent mode above 23,000 feet cabin altitude. In the 100 percent mode, the reference levels for warning and control follow the 263 mm Hg curve 152 or 93 percent oxygen curve 155 whichever is less.

Product gas oxygen concentration below the appropriate reference levels given for the regulator operating mode (Dilution or 100 percent) generates the low-oxygen signal 122 at the level comparator 118. The logic circuit 131 detects this low-oxygen signal and generates the warning signal on line 146. The warning signal activates the three-way solenoid controller 111 to de-energize the three-way solenoid valve 43 and light the warning lamp 93. In this event breathing gas is provided to the crew from the BOS plenum 17.

To summarize, the three-way solenoid valve 43 is deactivated to provide plenum gas to the crew members, and the warning signal 146 is activated when the concentrator output product composition drops below the level defined by the 263 mm Hg $PO_2$ curve 152 in FIG. 5 when the breathing regulators are operated in the 100 percent mode. The plenum gas is provided to the crew members and the warning signal 146 is provided when the concentrator product gas composition falls below the level defined by the 330 mm Hg $PO_2$ curve 151 and 90 percent oxygen curve 154 below 23,000 feet altitude when the breathing regulators are operated in the Dilution mode. The breathing regulators automatically switch over to the 100 percent mode above 23,000 feet as detected by the high altitude detector 117 independent of the position of the mode selection switch 89.

The oxygen monitor controller built-in test (BIT) function provides the capability to conduct a system self-test for preflight and an oxygen sensor calibration check for oxygen level maintenance. The purpose of the system preflight self-test is to ensure that the monitor controller is operating and provides a low-oxygen warning signal and automatically switches over to the plenum when the concentrator product gas composition drops below the minimum levels.

After the system has been on for a minimum 90 second warm-up time, a self-test can be initiated by momentarily pushing the BIT switch 88. Simultaneously the self-test timer 112 is started, the three-way BIT solenoid valve 42 is energized to allow air to flow through the sensor, and the BIT light 91 flashes to indicate that a self-test is in progress. Once the air reaches the oxygen sensor 66 the sensor output begins to drop approaching the warning level 157. For the self-test regardless of whether the regulator is in the Dilution or 100 percent mode, the mode selection with delay 113 signals the reference oxygen level approximation circuit 114 to provide the 263 mm Hg $PO_2$ warning level, V REF, to the level comparator. When the sensor output $VO_2$ drops below the warning level, the level comparator 118 provides a low-oxygen signal on line 122 to the logic circuit 131. The logic circuit in turn initiates the following:

a. Sends a signal to the input 139 of latch 133 to stop the flashing of the BIT light 91 indicating the test has been passed and momentarily activates flow from the BOS 17 and turns on the warning light 93 in the cockpit indicating low oxygen;

b. Resets the self-test timer 112; and c. Uses the output of the self-test timer to the OR gate 133 to de-energize the three-way self-test valve 42 allowing product gas to flow through the oxygen sensor 66.

The warning light 93 will be on briefly (less than five seconds) until the output 156 of the sensor 66 ($VO_2$) increases to above the warning level in route to the value corresponding to the product gas oxygen concentration.

Upon initiating a self-test, if the output 156 of the sensor 66 does not drop below the warning level 157 within 20 seconds as shown on FIG. 6, the self-test is considered as failed and the BIT light 91 will remain on as controlled by the latch 133 shown in FIG. 4.

A self-test is also initiated automatically at start-up by the power up circuit 137 which is activated by the power converter 107 and which provides a signal to the self-test timer 112. This test follows the same steps as above except the BIT light 91 is not energized unless the self-test fails.

The oxygen sensor calibration check is based on an air calibration and when passed verifies that the oxygen sensor output is calibrated over the 20-95 percent range in oxygen concentration. This test is initiated by means of the calibration check switch 75.

Upon initiating the check, the calibration check timer 132 generates a pulse to energize the three-way valve 42 in order to flow air through the oxygen sensor for two minutes and also to flash the BIT light 91 via the oscillator 136 and latch 133 to indicate that a calibration check is in progress. If during the test the output 156 of the sensor falls to within the calibration threshold between the values 162 and 163 as shown on FIG. 7, the CAL signal on line 123 is activated and the sensor has passed the calibration check.

After two minutes the calibration check timer 132 de-energizes the three-way valve 42 and allows the product gas to pass through the oxygen sensor 66. The warning light 93 will be on from the end of the calibration check until the output of the sensor 66 increases above the 263 mm Hg $PO_2$ warning level at which time the warning light 93 will turn off and the test will be complete.

If at the end of the two-minute calibration check the CAL signal on line 123 is not detected by the logic circuit 131 (thus meaning the output of the sensor 66 did not enter and remain within the calibration threshold), the sensor has failed the calibration check and the warning light 93 will remain on.

Having thus described the invention, various alterations and modifications will be apparent to those skilled in the art, which modifications and alterations are intended to be within the scope of the invention as defined by the appended claims.

What is claimed is:

1. A method for monitoring the oxygen concentration in a breathing gas for aircraft at a plurality of altitudes comprising the steps of:
   1. establishing a first curve $C_1$ representing minimum oxygen concentration at a plurality of altitudes;
   2. establishing a second curve $C_2$ of oxygen concentration at a plurality of altitudes for a first fixed partial pressure of oxygen ($P_1$), wherein the second curve $C_2$ is above the first curve $C_1$;
   3. monitoring the oxygen concentration of the breathing gas and the atmospheric pressure at the cockpit altitude and multiplying the two quantities together to give the product Pl
   4. comparing $P_1$ and P; and
   5. giving a signal indicating low oxygen concentration if P is less than $P_1$.

2. The method of claim 1 further comprising the step of:
   1. utilizing the method of claim 1 when using the breathing gas without dilution.

3. The method of claim 1 further comprising the step of:
   1. establishing a third curve $C_3$ of oxygen concentration at a plurality of altitudes for a second fixed partial pressure of oxygen $P_2$; wherein the third curve is above the first curve $C_1$ and the second curve $C_2$;
   2. comparing $P_2$ to P;
   3. giving a signal indicating low oxygen concentration if P is less than $P_2$.

4. The method of claim 3 further comprising the step of:
   1. utilizing the method of claim 3 when using the breathing gas with dilution.

5. An oxygen system for aircraft comprising:
   an oxygen concentrator in which pressurized air is alternately delivered by a rotary valve to a plurality of beds of molecular sieve material;
   a concentrator outlet which delivers oxygen enriched product gas from the molecular sieve beds;
   a plenum for storing oxygen enriched product gas from the concentrator outlet for use in the event of concentrator failure; and
   a pressure booster for increasing the pressure of product gas in the plenum in order to increase the amount of gas which is stored in the plenum, the pressure booster comprising:
   a driver piston and a compressor piston located in a driver cylinder and a compressor cylinder respectively;
   a rod rigidly coupling the driver piston to the compressor piston;
   a series of valves which control the flow of gas through the pressure booster;
   means for coupling air from the rotary valve in the concentrator to the driver cylinder;
   a pair of air inlets coupled to opposite ends of the driver cylinder;
   means for coupling enriched product gas from the concentrator outlet to the compressor cylinder, including a pair of product gas inlets coupled to opposite ends of the compressor cylinder whereby air from the rotary valve drives the driver piston and causes the compression piston to increase the pressure of the product gas for storage in the plenum and;
   a pair of product gas outlets coupled to opposite ends of the compressor cylinder.

6. The oxygen system of claim 5 wherein the series of valves comprises:
   a pair of one-way valves in the product gas inlets and a pair of one-way valves in the product gas outlets, wherein movement of the compressor piston away from one end of the compression cylinder causes intake of product gas into said one end and movement of the compressor piston toward said one end of the compression cylinder causes compression of product gas in said one end.

7. The oxygen system of claim 5 further comprising:
   an exhaust path for exhausting air from each end of the driver cylinder,
   a control valve in the exhaust path for controlling flow through the exhaust path, and
   a pressure tap coupling the plenum to the control valve, whereby a preselected pressure in the plenum causes the control valve to close the exhaust path to prevent operation of the driver piston.

8. An oxygen system for aircraft comprising:
   an oxygen concentrator in which pressurized air is alternately delivered by a rotary valve to a plurality of beds of molecular sieve material;
   a concentrator outlet which delivers oxygen enriched product gas from the molecular sieve beds;
   a plenum for storing oxygen enriched product gas from the concentrator outlet for use in the event of concentrator failure;
   a pressure booster for increasing the pressure of product gas in the plenum in order to increase the amount of product gas which is stored in the plenum;
   oxygen sensor means for measuring the oxygen concentration of the product gas; and plenum fill valve means controlled by the oxygen sensor means for controlling delivery of product gas to the plenum, said plenum fill valve means delivering product gas to the plenum for storage only when oxygen concentration of the product gas is greater than a preselected reference level.

9. The oxygen system of claim 8 further comprising:
conduit means for coupling the oxygen sensor means to product gas from the concentrator;
a flow restrictor in the conduit means for isolating the oxygen sensor from sudden pressure variations; and
an absolute pressure regulator which maintains a constant pressure at the oxygen sensor means in order to avoid ambient pressure dependent fluctuations in the oxygen sensor output.

10. The oxygen system of claim 9 further comprising:
a heater means for maintaining the oxygen sensor means at a preselected temperature range independent of ambient temperature.

11. An oxygen system for aircraft comprising:
an oxygen concentrator in which pressurized air is alternately delivered by a rotary valve to a plurality of beds of molecular sieve material;
a concentrator outlet which delivers oxygen enriched product gas from the molecular sieve beds;
a plenum for storing oxygen enriched product gas from the concentrator outlet for use in the event of concentrator failure;
a pressure booster for increasing the pressure of product gas in the plenum in order to increase the amount of gas which is stored in the plenum; and
means for delivering product gas from the plenum for use in the aircraft when the oxygen concentration of product gas from the concentrator is less than aircraft breathing requirements comprising a product delivery valve which delivers product gas from either the concentrator outlet or the plenum and an oxygen sensor means for controlling the product delivery valve.

12. The oxygen system of claim 11 further comprising:
conduit means for coupling the oxygen sensor means to product gas from the concentrator;
a flow restrictor in the conduit means for isolating the oxygen sensor from sudden pressure variations; and
an absolute pressure regulator which maintains a constant pressure at the oxygen sensor means in order to avoid ambient pressure dependent fluctuations in the oxygen sensor output.

13. The oxygen system of claim 12 further comprising:
a heater means for maintaining the oxygen sensor means at a preselected temperature range independent of ambient temperature.

14. An oxygen system for aircraft comprising:
an oxygen concentrator in which pressurized air is alternately delivered by a rotary valve to a plurality of beds of molecular sieve material;
a concentrator outlet which delivers oxygen enriched product gas from the molecular sieve beds;
a plenum for storing oxygen enriched product gas from the concentrator outlet for use in the event of concentrator failure;
means for delivering product gas to the plenum for storage only when oxygen concentration of the product gas is greater than a preselected reference level;
means for delivering product gas from the plenum for use in the aircraft when the oxygen concentration of product gas from the concentrator is less than aircraft breathing requirements;
a product deliver valve which delivers product gas from either the concentrator output or the plenum and an oxygen sensor means for measuring oxygen concentration in the product gas and for controlling the product delivery valve; and
a pressure booster for increasing the pressure of product gas in the plenum in order to increase the amount of gas which is stored in the plenum, the pressure booster comprising:
a driver piston and a compressor piston located in a driver cylinder and a compressor cylinder respectively;
a rod rigidly coupling the driver piston to the compressor piston;
a series of valves which control the flow of gases through the pressure booster;
means for coupling air from the rotary valve in the concentrator to the driver cylinder; and
means for coupling enriched product gas from the concentrator outlet to the compression cylinder, whereby air form the rotary valve drives the driver piston and causes the compression piston to increase the pressure of the product gas for storage in the plenum.

15. The oxygen system of claim 14 further comprising:
conduit means for coupling the oxygen sensor means to product gas from the concentrator;
a flow restrictor in the conduit means for isolating the oxygen sensor from sudden pressure variations; and
an absolute pressure regulator which maintains a constant pressure at the oxygen sensor means in order to avoid ambient pressure dependent fluctuations in the oxygen sensor output.

16. The oxygen system of claim 15 further comprising: a
heater means for maintaining the oxygen sensor means at a preselected temperature range independent of ambient temperature.

17. An oxygen system for aircraft comprising:
an oxygen concentrator in which pressurized air is alternately delivered by a rotary valve to a plurality of beds of molecular sieve material;
a concentrator outlet which delivers oxygen enriched product gas from the molecular sieve beds;
a plenum for storing oxygen enriched product gas from the concentrator outlet for use in the event of concentrator failure;
a pressure booster for increasing the pressure of product gas in the plenum in order to increase the amount of product gas which is stored in the plenum;
means for delivering product gas to the plenum for storage only when oxygen concentration of the product gas is greater than a preselected reference level;
oxygen sensor means for measuring the oxygen concentration of the product gas;
a heater means for maintaining the oxygen sensor means at a preselected temperature range independent of ambient temperature;

conduit means for coupling the oxygen sensor means to product gas from the concentrator;

a flow restrictor in the conduit means for isolating the oxygen sensor from sudden pressure variations; and an absolute pressure regulator which maintains a constant pressure at the oxygen sensor means in order to avoid ambient pressure dependent fluctuations in the oxygen sensor output.

18. The oxygen system of claim 17 wherein the preselected temperature range is between 400° C. and 600 C.

19. The oxygen system of claim 18 wherein the oxygen sensor means comprises a zirconia electrolyte element.

20. An oxygen system for aircraft comprising:

an oxygen concentrator in which pressurized air is alternately delivered by a rotary valve to a plurality of beds of molecular sieve material;

a concentrator outlet which delivers oxygen enriched product gas form the molecular sieve beds;

a plenum for storing oxygen enriched product gas from the concentrator outlet for use in the event of concentrator failure;

a pressure booster for increasing the pressure of product gas in the plenum in order to increase the amount of gas which is stored in the plenum; and means for delivering product gas from the plenum for use in the aircraft when the oxygen concentration of product gas from the concentrator is less than aircraft breathing requirements;

a product delivery valve which delivers product gas from either the concentrator outlet or the plenum;

an oxygen sensor means for controlling the product delivery valve;

a heater means for maintaining the oxygen sensor means at a preselected temperature range independent of ambient temperature;

conduit means for coupling the oxygen sensor means to product gas from the concentrator;

a flow restrictor in the conduit means for isolating the oxygen sensor from sudden pressure variations; and an absolute pressure regulator which maintains a constant pressure at the oxygen sensor means in order to avoid ambient pressure dependent fluctuations in the oxygen sensor output.

21. The oxygen system of claim 20 wherein the preselected temperature range is between 400° C. and 600° C.

22. The oxygen system of claim 21 wherein the oxygen sensor means comprises a zirconia electrolyte element.

23. An oxygen system for aircraft comprising:

an oxygen concentrator in which pressurized air is alternately delivered by a rotary valve to a plurality of beds of molecular sieve material;

a concentrator outlet which delivers oxygen enriched product gas from the molecular sieve beds;

a plenum for storing oxygen enriched product gas from the concentrator outlet for use in the event of concentrator failure;

a product delivery valve which delivers product gas from either the concentrator outlet or the plenum;

an oxygen sensor means for measuring oxygen concentration in the product gas and for controlling the product delivery valve;

heater means for maintaining the oxygen sensor means at a preselected temperature range independent of ambient temperature;

conduit means for coupling the oxygen sensor means to product gas from the concentrator;

a flow restrictor in the conduit means for isolating the oxygen sensor from sudden pressure variations;

an absolute pressure regulator which maintains a constant pressure at the oxygen sensor means in order to avoid ambient pressure dependent fluctuations in the oxygen sensor output;

means for delivering product gas to the plenum for storage only when oxygen concentration of the product gas is greater than a preselected reference level;

means for delivering product gas from the plenum for use in the aircraft when the oxygen concentration of product gas from the concentrator is less than aircraft breathing requirements; and a pressure booster for increasing the pressure of product gas in the plenum in order to increase the amount of gas which is stored in the plenum, the pressure booster comprising:

a driver piston and a compressor piston located in a driver cylinder and a compressor cylinder respectively;

a rod rigidly coupling the driver piston to the compressor piston;

a series of valves which control the flow of gases through the pressure booster;

means for coupling air from the rotary valve in the concentrator to the driver cylinder; and means for coupling enriched product gas from the concentrator outlet to the compression cylinder, whereby air form the rotary valve drives the driver piston and causes the compression piston to increase the pressure of the product gas for storage in the plenum.

24. The oxygen system of claim 23 wherein the oxygen sensor means comprises a zirconia electrolyte element.

* * * * *